US012788873B2

(12) United States Patent
Gyory et al.

(10) Patent No.: US 12,788,873 B2
(45) Date of Patent: Nov. 10, 2026

(54) PRECISION PUMP WITH AUTOMATIC VALVE SWITCHING AND LOW TOLERANCE STACK-UP USING SIDE PORTED CANNULA FOR SMALL VOLUME PUMPING

(71) Applicant: Becton, Dickinson and Company, Franklin Lakes, NJ (US)

(72) Inventors: John Richard Gyory, Sudbury, MA (US); Eric Ray Sun, Medford, MA (US); Alessandro E Pizzochero, Chelmsford, MA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 965 days.

(21) Appl. No.: 17/995,244

(22) PCT Filed: Mar. 31, 2021

(86) PCT No.: PCT/US2021/025178
§ 371 (c)(1),
(2) Date: Sep. 30, 2022

(87) PCT Pub. No.: WO2021/202737
PCT Pub. Date: Oct. 7, 2021

(65) Prior Publication Data

US 2023/0321341 A1 Oct. 12, 2023

Related U.S. Application Data

(60) Provisional application No. 63/005,114, filed on Apr. 3, 2020.

(51) Int. Cl.
*A61M 5/142* (2006.01)
*F04B 7/06* (2006.01)
(Continued)

(52) U.S. Cl.
CPC ........... *A61M 5/14216* (2013.01); *F04B 7/06* (2013.01); *F04B 9/042* (2013.01); *F04B 13/00* (2013.01)

(58) Field of Classification Search
CPC .......... A61M 5/14216; A61M 5/16809; A61M 5/14248; F04B 7/06; F04B 9/042; F04B 13/00
See application file for complete search history.

(56) References Cited

U.S. PATENT DOCUMENTS 5,494,420 A 2/1996 Mawhirt et al.
2006/0053830 A1 3/2006 Adams
(Continued)

FOREIGN PATENT DOCUMENTS

JP 2016-525182 A 8/2016
WO 2013046156 A1 4/2013

*Primary Examiner* — James D Ponton
(74) *Attorney, Agent, or Firm* — Dickinson Wright, PLLC

(57) ABSTRACT

A pump for the pumping small volumes of medical fluid is provided. The pump has a manifold chamber having an inlet port and an outlet port. Within the manifold chamber, a cannula having input and output holes oriented with respect to the inlet and outlet ports is rotated within the manifold chamber, and translated axially in a reciprocating manner. The input opening of the cannula overlaps with the inlet port as the manifold chamber volume is increasing to draw fluid into the manifold chamber from the input port. The output opening of the cannula chamber overlaps with the output port as the manifold chamber volume is decreasing to force fluid out of the manifold chamber to the outlet port. The cannula may be formed from metal needle stock.

11 Claims, 13 Drawing Sheets

(51) Int. Cl.
*F04B 9/04* (2006.01)
*F04B 13/00* (2006.01)

(56) References Cited

U.S. PATENT DOCUMENTS

2016/0160854 A1* 6/2016 Dehan ........................ F04B 7/06
417/494
2017/0184091 A1 6/2017 Focht et al.

* cited by examiner

PRECISION PUMP WITH AUTOMATIC VALVE SWITCHING AND LOW TOLERANCE STACK-UP USING SIDE PORTED CANNULA FOR SMALL VOLUME PUMPING

CROSS-REFERENCE TO RELATED APPLICATIONS

This application claims priority to International Application No. PCT/US2021/025178, filed Mar. 31, 2021 and Provisional Application No. 63/005,114, filed Apr. 3, 2020.

FIELD OF THE INVENTION

The present invention relates generally to a compact, precise, reliable and low cost pump suitable for subcutaneous delivery of a liquid pharmaceutical product. More particularly, embodiments of the present invention relate to a pump with a side ported cannula that reciprocates during rotation according to a cam surface to pump a fluid by displacement. The pharmaceutical product to be delivered may be insulin for diabetic patients.

BACKGROUND OF THE INVENTION

Diabetes is a group of diseases marked by high levels of blood glucose resulting from defects in insulin production, insulin action, or both. There are 23.6 million people in the United States, or 8% of the population, who have diabetes. The total prevalence of diabetes has increased 13.5% since the 2005-2007 time period. Diabetes can lead to serious complications and premature death, but there are well-known products available for people with diabetes to help control the disease and lower the risk of complications.

Treatment options for people with diabetes include specialized diets, oral medications and/or insulin therapy. The primary goal for diabetes treatment is to control the patient's blood glucose (sugar) level in order to increase the chances of a complication-free life. It is not always easy, however, to achieve good diabetes management, while balancing other life demands and circumstances.

Currently, there are two principal modes of daily insulin therapy for the treatment of type 1 diabetes. The first mode includes syringes and insulin pens that require a needle stick at each injection, typically three to four times per day that are simple to use and relatively low in cost. Another widely adopted and effective method of treatment for managing diabetes is the use of an insulin pump. Insulin pumps can help the user keep blood glucose levels within target ranges based on individual needs, by continuous infusion of insulin. By using an insulin pump, the user can match insulin therapy to lifestyle, rather than matching lifestyle to how an insulin injection is working for the user.

Conventional insulin pumps are capable of delivering rapid or short-acting insulin 24 hours a day through a catheter placed under the skin. Insulin doses are typically administered at a basal rate and in a bolus dose. Basal insulin is delivered continuously over 24 hours, and keeps the user's blood glucose levels in a consistent range between meals and overnight. Some insulin pumps are capable of programming the basal rate of insulin to vary according to the different times of the day and night. Bolus doses are typically administered when the user takes a meal, and generally provide a single additional insulin injection to balance the carbohydrates consumed. Some conventional insulin pumps enable the user to program the volume of the bolus dose in accordance with the size or type of the meal consumed. Conventional insulin pumps also enable a user to take in a correctional or supplemental bolus of insulin to compensate for a low blood glucose level at the time the user is calculating a meal bolus.

There are many advantages of conventional insulin pumps over other methods of diabetes treatment. Insulin pumps deliver insulin over time rather than in single injections and thus typically result in less variation within the blood glucose range that is recommended by the American Diabetes Association. Conventional insulin pumps also reduce the number of needle sticks which the patient must endure, and make diabetes management easier and more effective for the user, thus considerably enhancing the quality of the user's life.

A major disadvantage of existing insulin pumps is that, in spite of their portability, they include multiple components and can be heavy and cumbersome to use. They are also typically more expensive than other methods of treatment. From a lifestyle standpoint, the conventional pump with its associated tubing and infusion set can be inconvenient and bothersome for the user.

Unlike a conventional infusion pump, a patch pump is an integrated device that combines most or all of the fluidic components, including the fluid reservoir, pumping mechanism and a mechanism for automatically inserting the cannula, in a single housing which is adhesively attached to an infusion site on the patient's skin, and does not require the use of a separate infusion or tubing set. Some patch pumps wirelessly communicate with a separate controller (as in one device sold by Insulet Corporation under the brand name OmniPod®), while others are completely self-contained. Such devices are replaced on a frequent basis, such as every three days, when the insulin supply is exhausted.

As a patch pump is designed to be a self-contained unit that is worn by the diabetic patient, it is preferable to be as small as possible so that it does not interfere with the activities of the user. In order to minimize discomfort to the user, it is preferable to minimize the overall dimension of the patch pump. However, in order to minimize the overall dimensions of the patch pump, its constituent parts should be reduced in size as much as possible.

Accordingly, there is a need in the art for a liquid pump that is precise, compact and cost-effective, so that it can be provided as part of a disposable system such as a patch pump.

It is an object of exemplary embodiment of the present invention to provide a precise, compact, cost-effective pump for a wearable medical device, so that more diabetes patients can benefit from the advantages these devices provide.

SUMMARY OF THE INVENTION

According to one embodiment of the present invention, there is provided a pump for the pumping of a liquid, said pump comprising a manifold chamber having an inlet port and an outlet port. Within the manifold chamber, a cannula having input and output holes oriented with respect to the inlet and outlet ports is rotated within the manifold chamber, and translated axially in a reciprocating manner. The input opening of the cannula overlaps with the inlet port as the manifold chamber volume is increasing to draw fluid into the manifold chamber from the input port. The output opening of the cannula chamber overlaps with the output port as the manifold chamber volume is decreasing to force fluid out of the manifold chamber to the outlet port.

An advantage of a pump according to an embodiment of the present invention is that very small and precise amounts of liquid medicament can be pumped per revolution of the side ported cannula. The cannula may be formed from very precise gauge needle stock, and reciprocate a very precise distance. This enables small liquid dosages to be injected very precisely, with reduced tolerance stack-up, and fewer materials coming into contact with the pharmaceutical liquid.

BRIEF DESCRIPTION OF THE DRAWINGS

The above and other exemplary objects, features and advantages of the present invention will become more apparent from the following description of certain exemplary embodiments thereof when taken in conjunction with the accompanying drawings, in which.

Throughout the drawings, like reference numerals will be understood to refer to like elements, features and structures.

DETAILED DESCRIPTION OF EXEMPLARY EMBODIMENTS

The matters exemplified in this description are provided to assist in an understanding of exemplary embodiments of the invention, and are made with reference to the accompanying drawings. Descriptions of well-known functions and constructions are omitted for clarity and conciseness.

Figure 1:
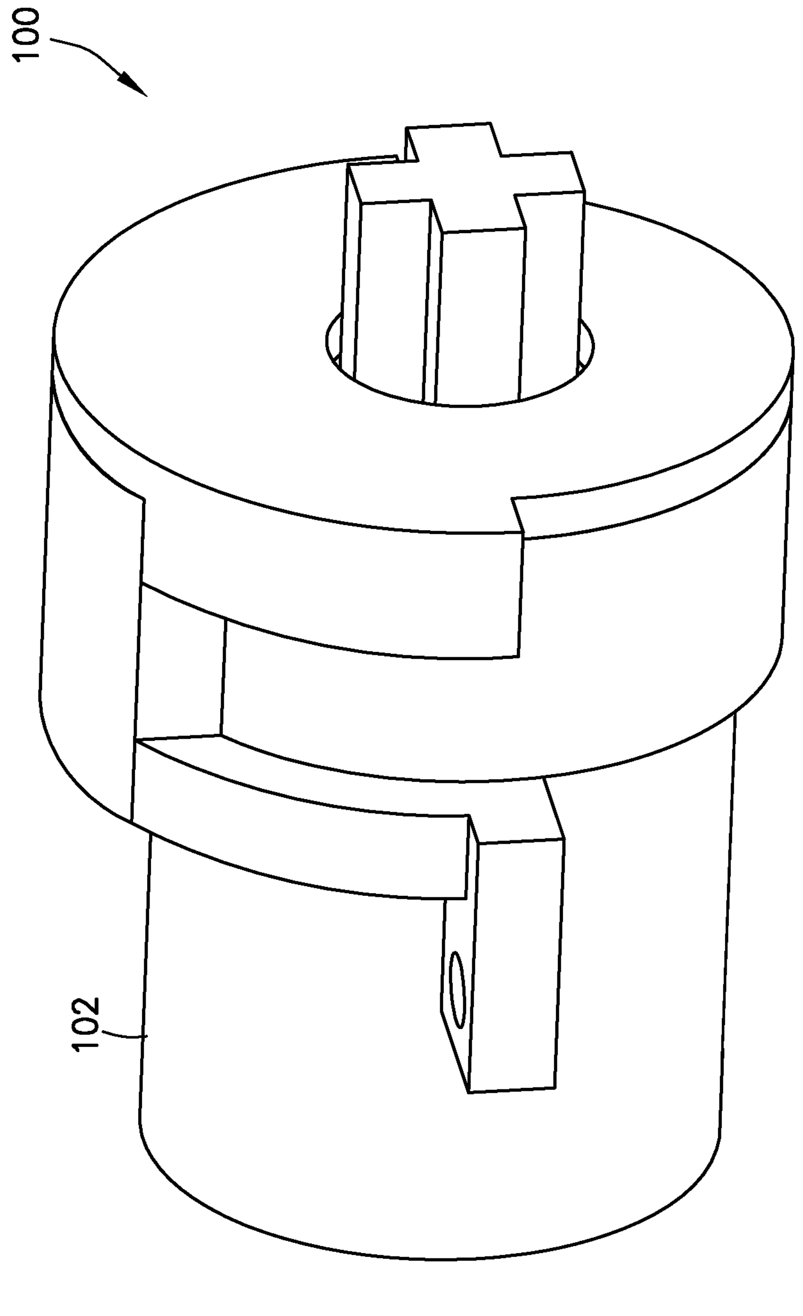
FIG. 1 is an isometric view of a pump according to an exemplary embodiment of the invention.
Figure 2:
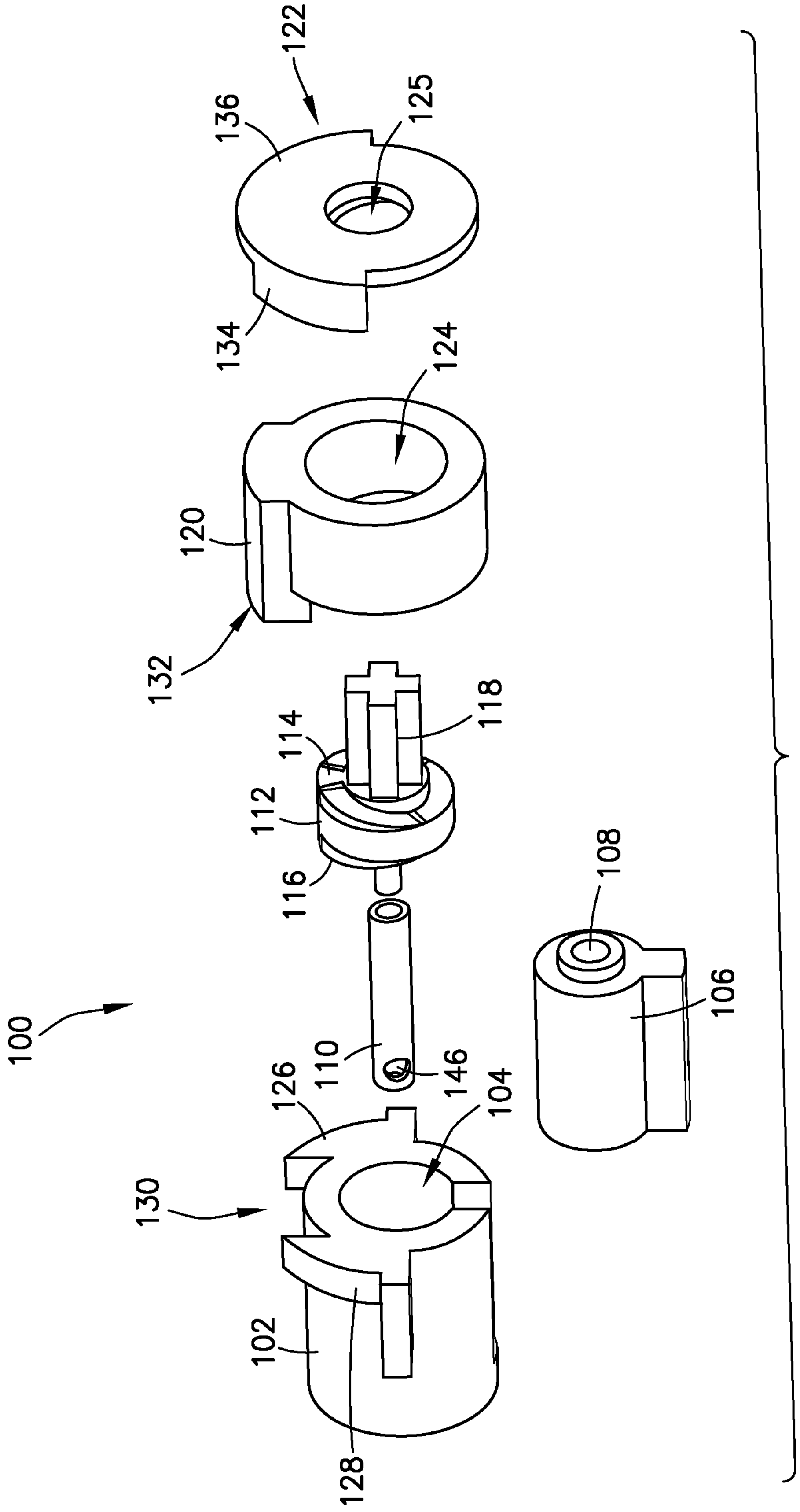
FIG. 2 is an exploded view of a pump according to an exemplary embodiment of the invention.

Turning now to FIGS. 1 and 2, the components of the micro pump according to an exemplary embodiment of the invention, and how they are assembled will be described in further detail. The micro pump 100 includes a main housing 102. The main housing 102 includes a pump chamber 104. A manifold 106 is received into the pump chamber 104. The manifold 106 includes cannula chamber 108 in which cannula 110 rotates and reciprocates axially. Cannula 110 is fixed to cam body 112. Cam body 112 includes proximal cam surface 114 and distal cam surface 116 as well as motor coupling 118. Cam chamber housing 120 and cam chamber cap 122 form the cam chamber 124 in which cam 112 is received. Cam chamber cap 122 also includes opening 125 through which motor coupling 118 extends.

As illustrated main housing 102, cam chamber housing 120 and cam chamber cap 122 include corresponding boss features which prevent relative rotational movement once assembled. Main housing 102 includes bosses 126 and 128 which have a space 130 therebetween. Cam chamber housing 120 includes a boss 132 that is received into opening 130 and abuts bosses 126 and 128. Cam chamber cap 122 includes bosses 134 and 136 which are spaced apart so that boss 132 may be received between them and abut one another.

Figure 3:
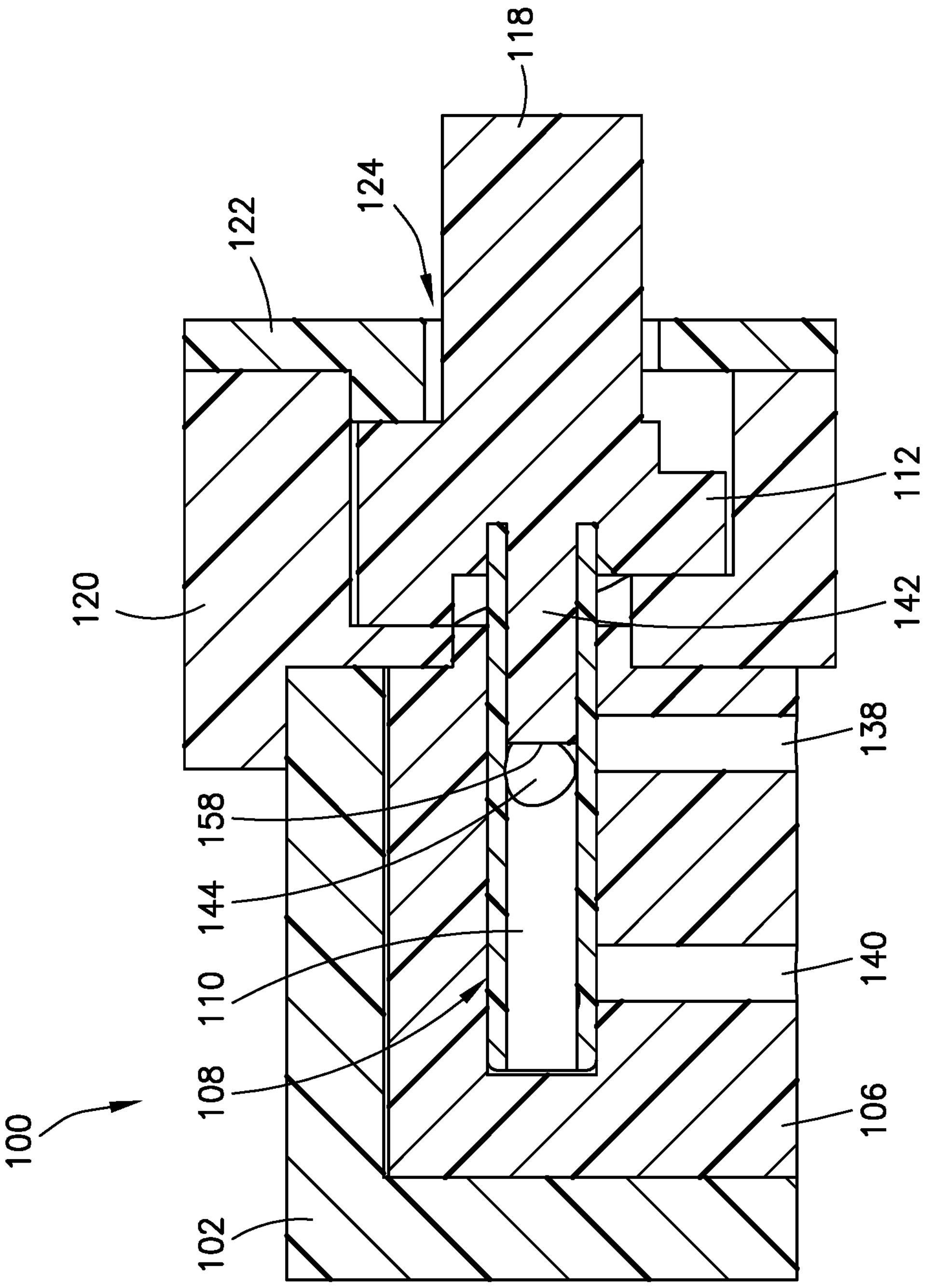
FIG. 3 is a side cross sectional view of a pump according to an exemplary embodiment of the invention.
Figure 4:
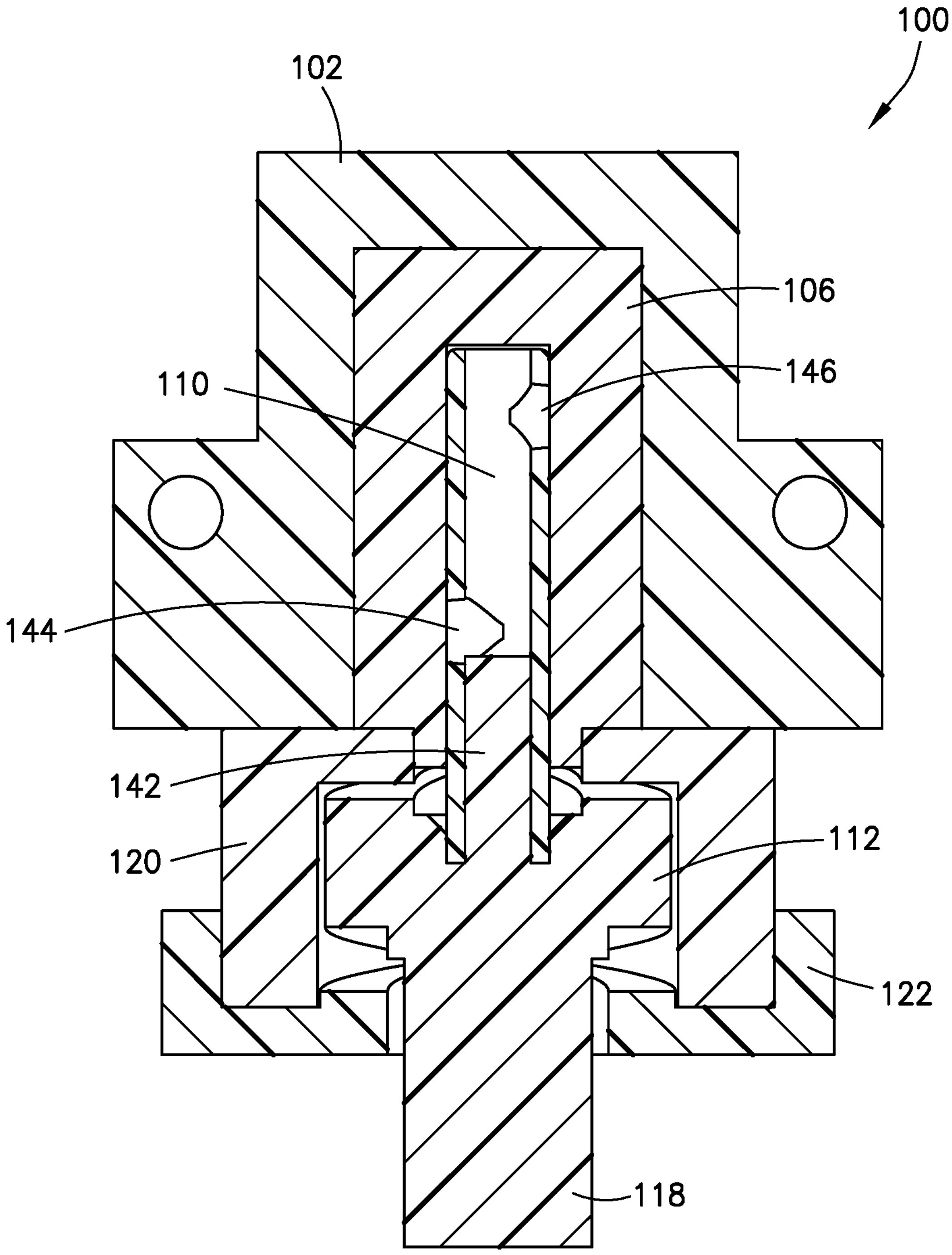
FIG. 4 is a top cross sectional view according to an exemplary embodiment of the invention.

Turning now to FIGS. 3 and 4, which are side and bottom cross-sectional views of micro pump 100, respectively, according to an exemplary embodiment of the invention, further aspects and components of the micro pump 100 member will now be described. As illustrated in FIG. 3, manifold 106 includes an input port 138 and an output port 140. Both ports 138, 140 connect to manifold chamber 108. It should be noted that cannula 110 fits within manifold chamber 18 substantially snugly. It should also be noted that main housing 102, cam chamber housing 120 and cam chamber cap 122 form a substantially liquid-tight chamber in which cannula 110 can rotate and reciprocate. As can be seen from FIGS. 3 and 4 cannula 110 is mounted on a stem 142 of the cam 112. The cannula 110 is preferably fixed to the stem 142 by any conventional means known including sonic welding, frictional engagement, adhesive, or any other suitable fixation method. Turning to FIG. 4, it can be seen that cannula 110 is provided with an input hole 144 and an output hole 146. Cannula input hole 144 is provided in a side wall of the cannula 110 in a proximal portion of the cannula. Output hole 146 is provided at a distal portion of the cannula 110 and on an opposite side of the side wall from input hole 144. Input hole 144 is arranged to overlap input port 138 during a portion of the movement of the cam assembly and output hole 146 is positioned overlap output hole 140 during a different portion of the rotational movement of the cam 112. The relative rotation and reciprocation of the cannula 110 within chamber 108 according to interaction with cam surfaces 114, 116 of the cam 112 within the cam chamber housing 120 and the cam chamber cap 122 will be described in further detail below.

Figure 5:
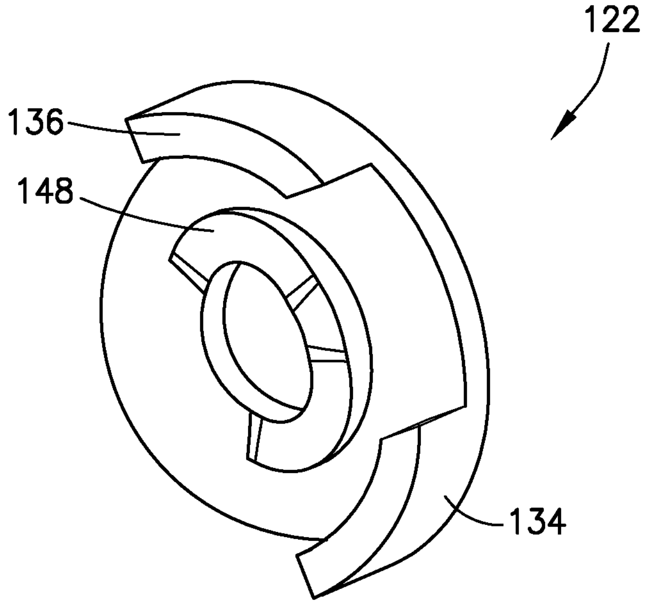
FIG. 5 is an isometric view of a cam chamber cap according to an exemplary embodiment of the invention.

FIG. 5 is an isometric view of cam chamber cap 122. Cam chamber cap bosses 134 and 136 are illustrated to be separated from one another and provided in an outside portion of the cam chamber cap 122. Cam chamber cap cam surface 148 is provided within cam chamber cap 22 to interact with cam surface 114 of the cam 112.

Figure 6:
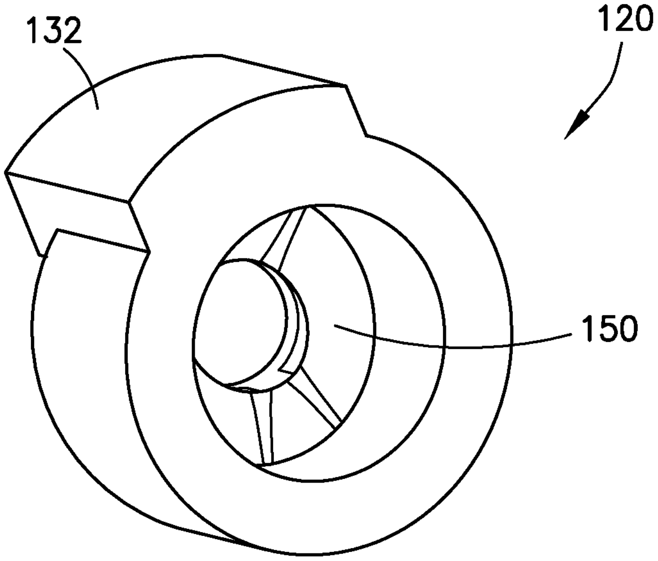
FIG. 6 is an isometric of a cam chamber housing according to an exemplary embodiment of the invention.

FIG. 6 illustrates an isometric view of the cam chamber housing 120. Cam chamber housing boss 132 is provided on an outer portion of the cam chamber housing 120 and fits between cam chamber cap bosses 134 and 136 prevent cam chamber cup 122 from rotating relative to cam chamber housing 120 once the micro pump 100 is assembled. Also illustrated in FIG. 6 is cam chamber housing cam surface 150 which interacts with cam surface 116 of the cam 112, as will be described in further detail below.

Figure 7:
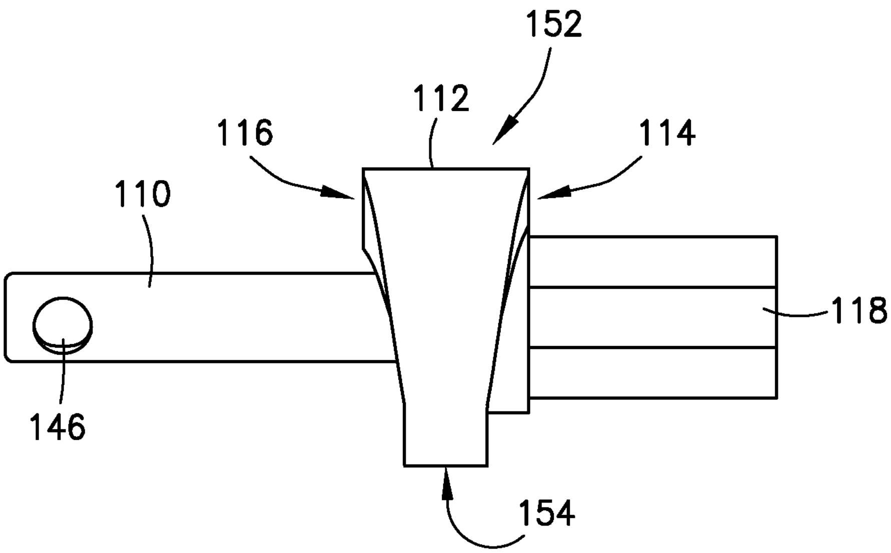
FIG. 7 is a side view of a cannula assembly according to an exemplary embodiment of the invention.
Figure 8:
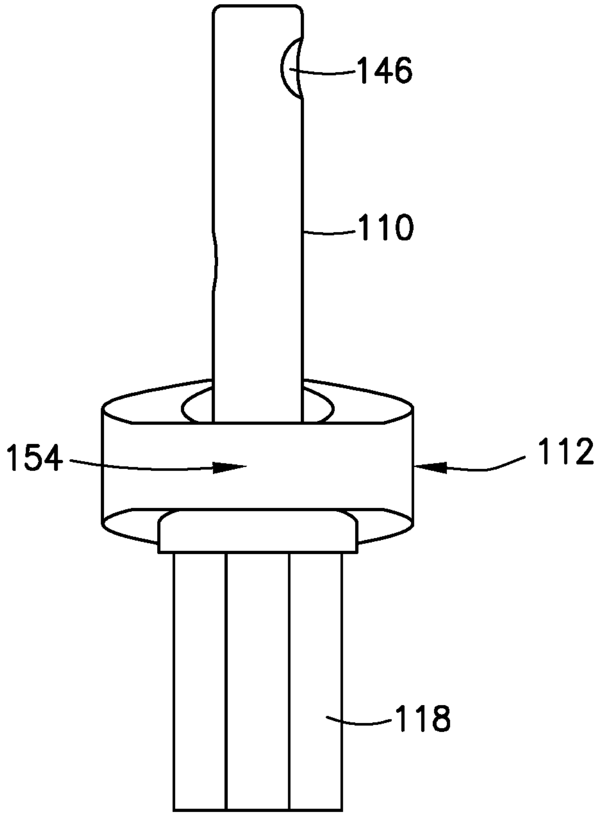
FIG. 8 is a bottom view of the cannula assembly according to an exemplary embodiment of the invention.

FIG. 7 illustrates a side view of the cam 112. The cam 112 includes a proximal cam service 114 and a distal cam service 116. As can be seen the cam surfaces have corresponding slanted surfaces which will interact with cam chamber cap cam surface 148 cam chamber housing cam service 150, respectively, to cause the cannula 110 to translate back and forth in an axial direction as the cam 112 is rotated by a motor attached to motor coupling 118. As can be seen in FIG. 7 and also in bottom view of the cam 112 shown in FIG. 8, the cam 112 includes a wide portion 152 and a narrow portion 154.

Figure 9:
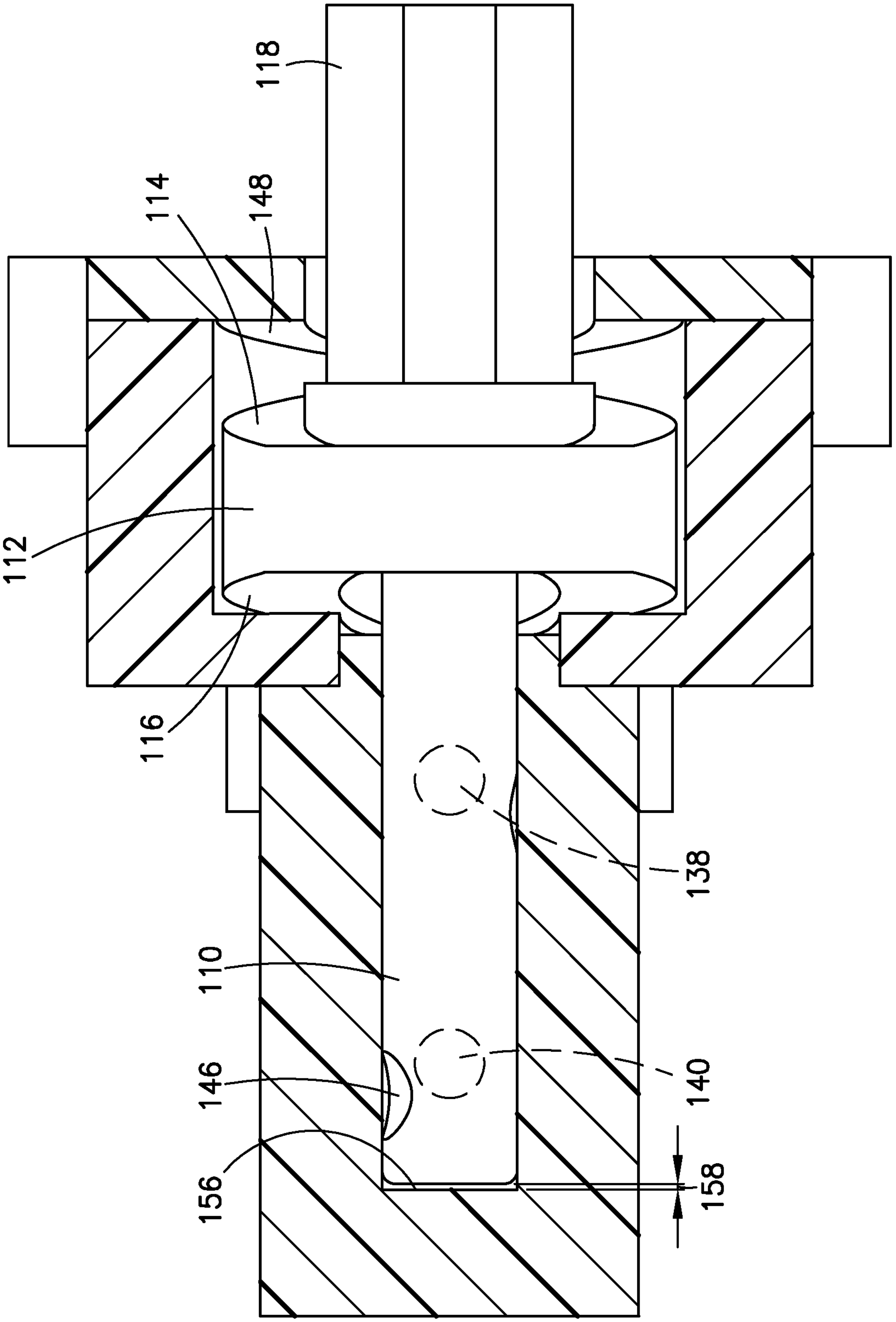
FIGS. 9-15 illustrate various operational states of the micro pump according to an exemplary embodiment of the invention.
Figure 10:
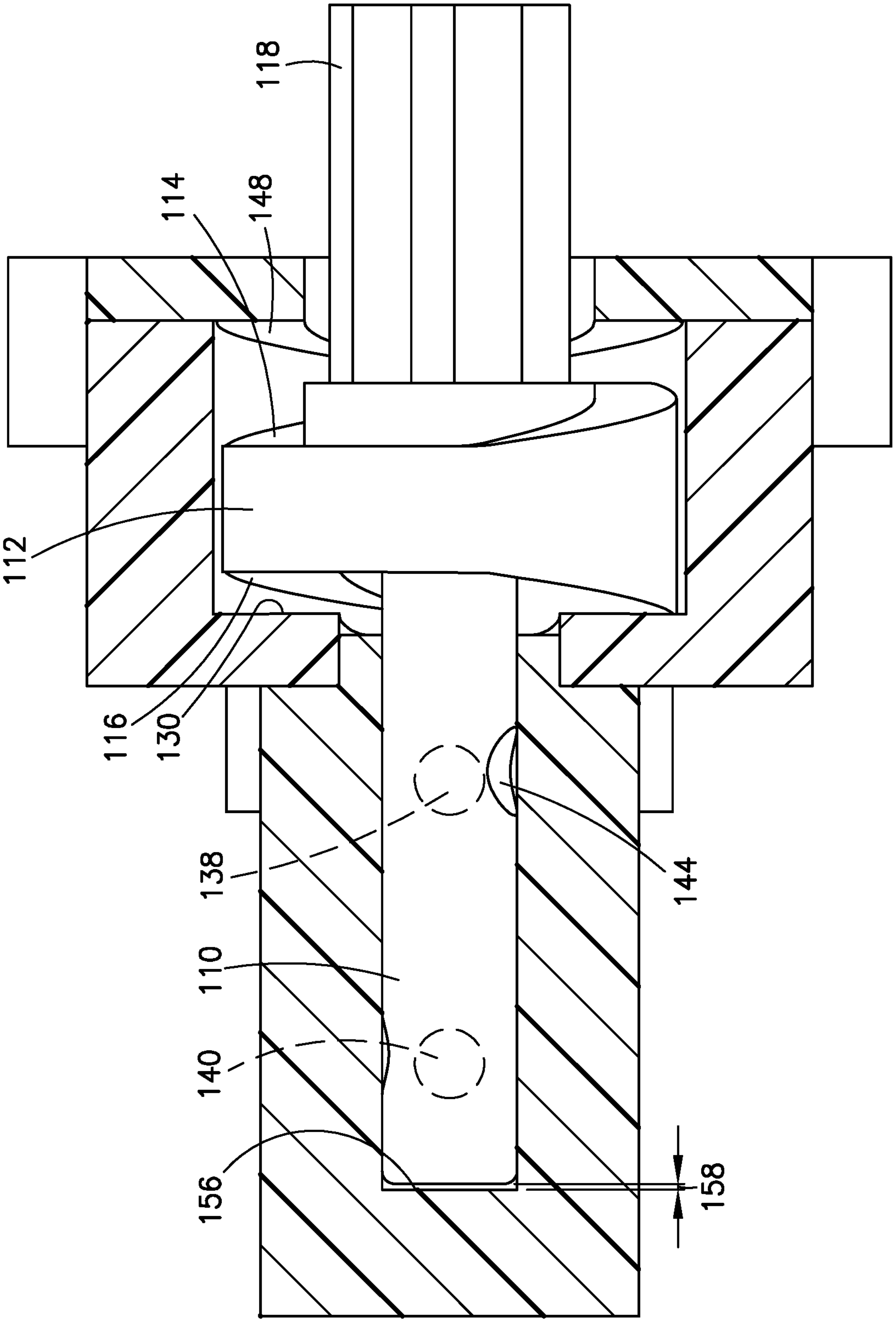
Figure 11:
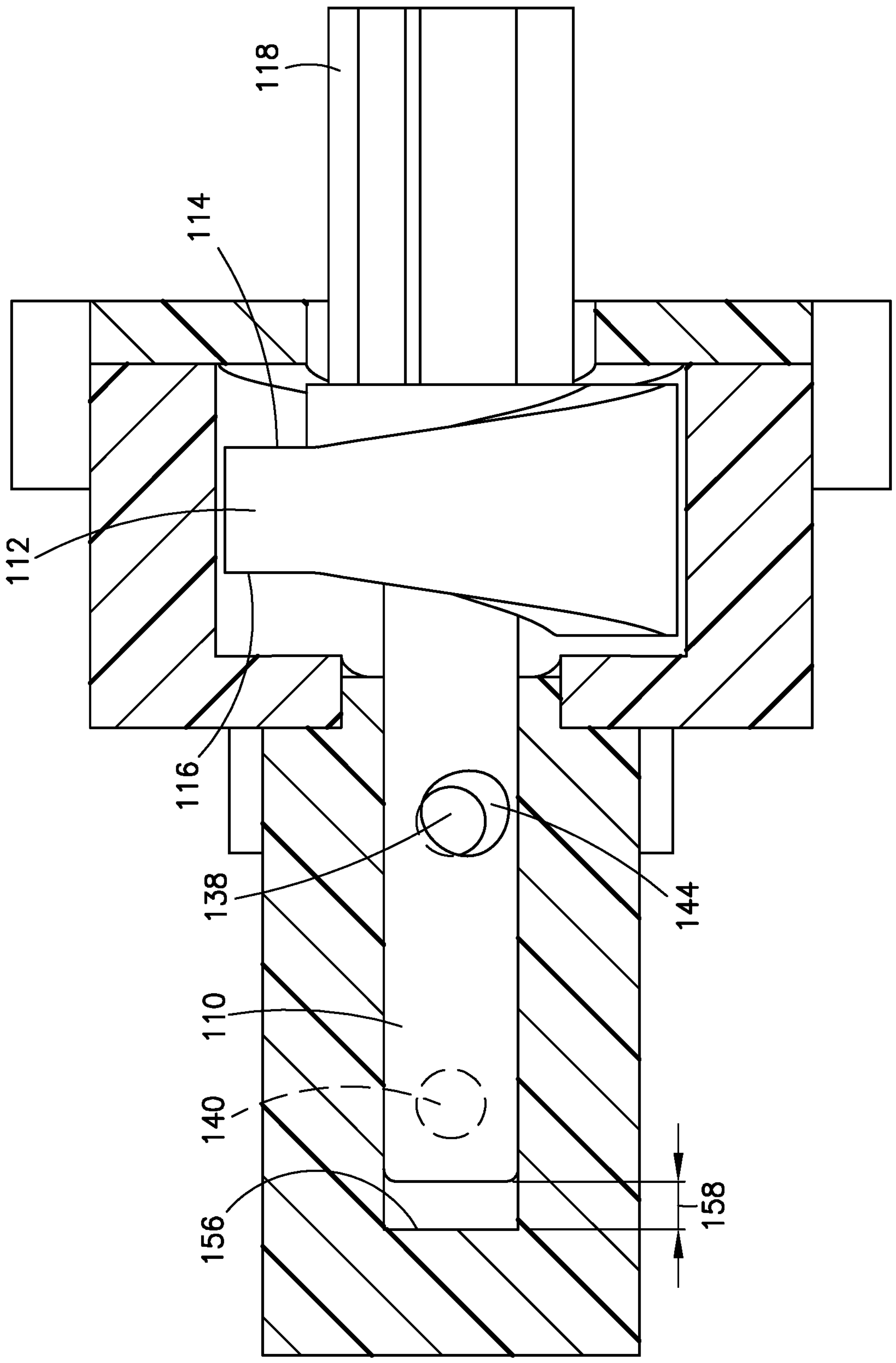
Figure 12:
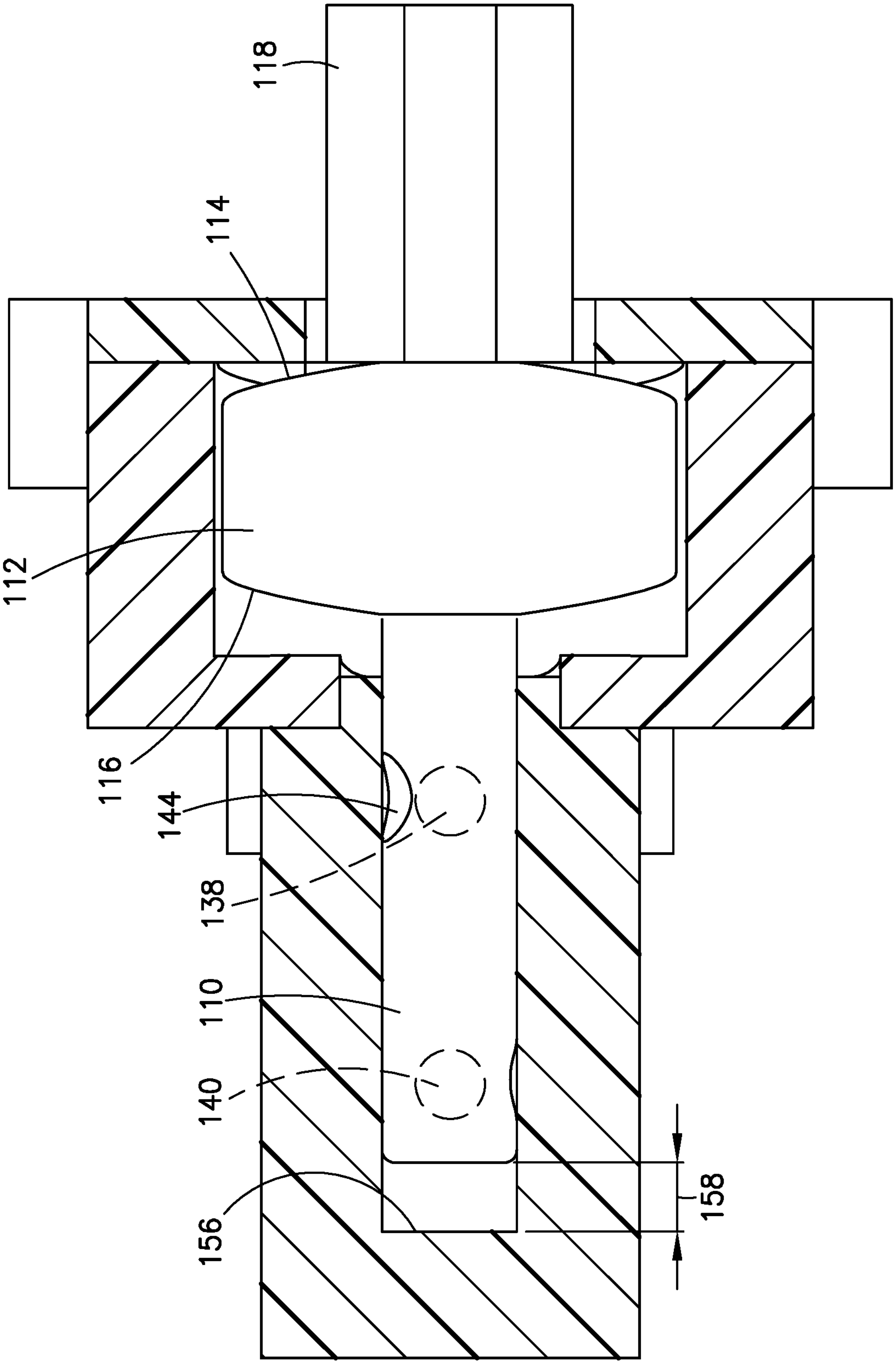
Figure 13:
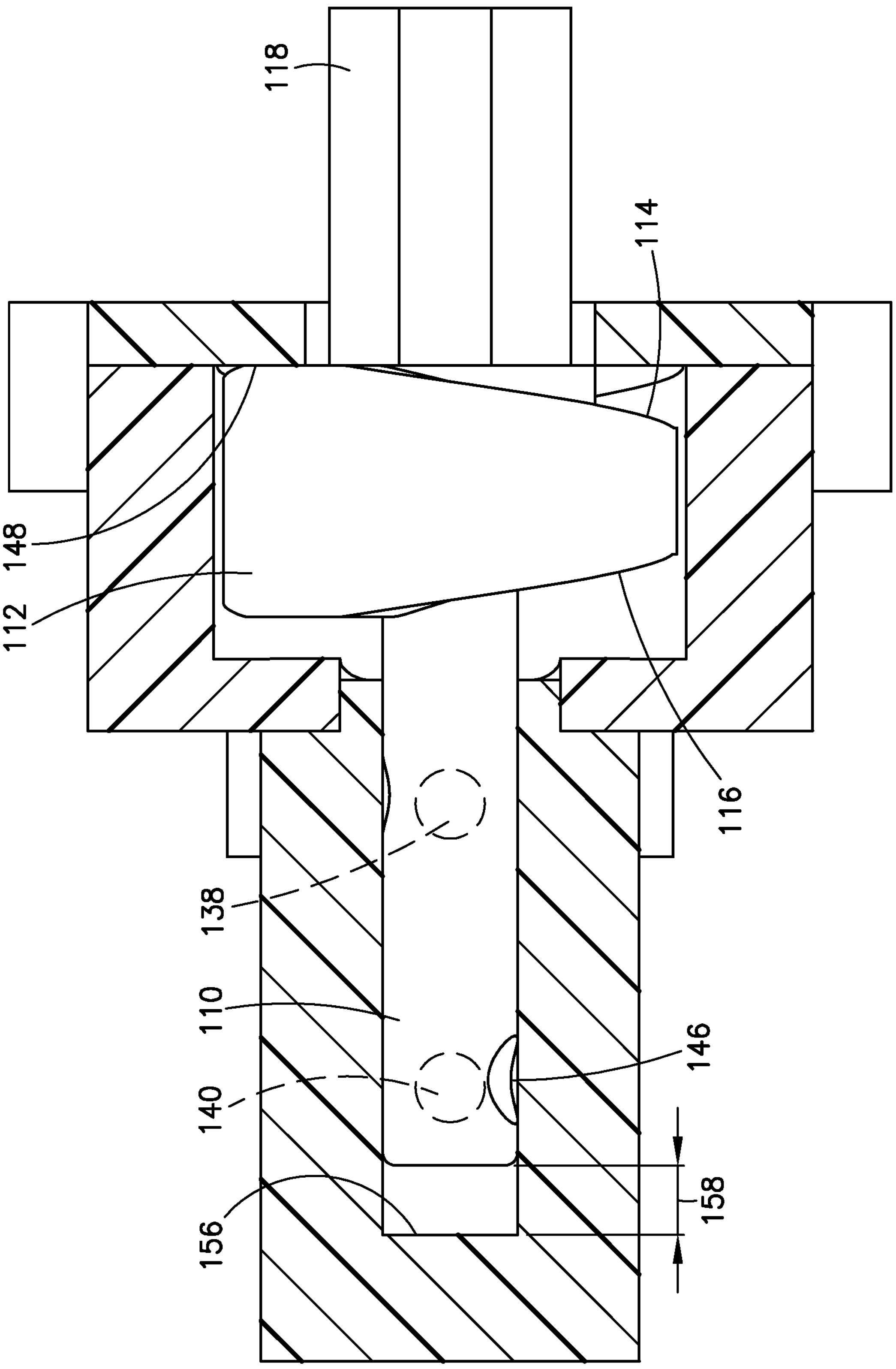
Figure 14:
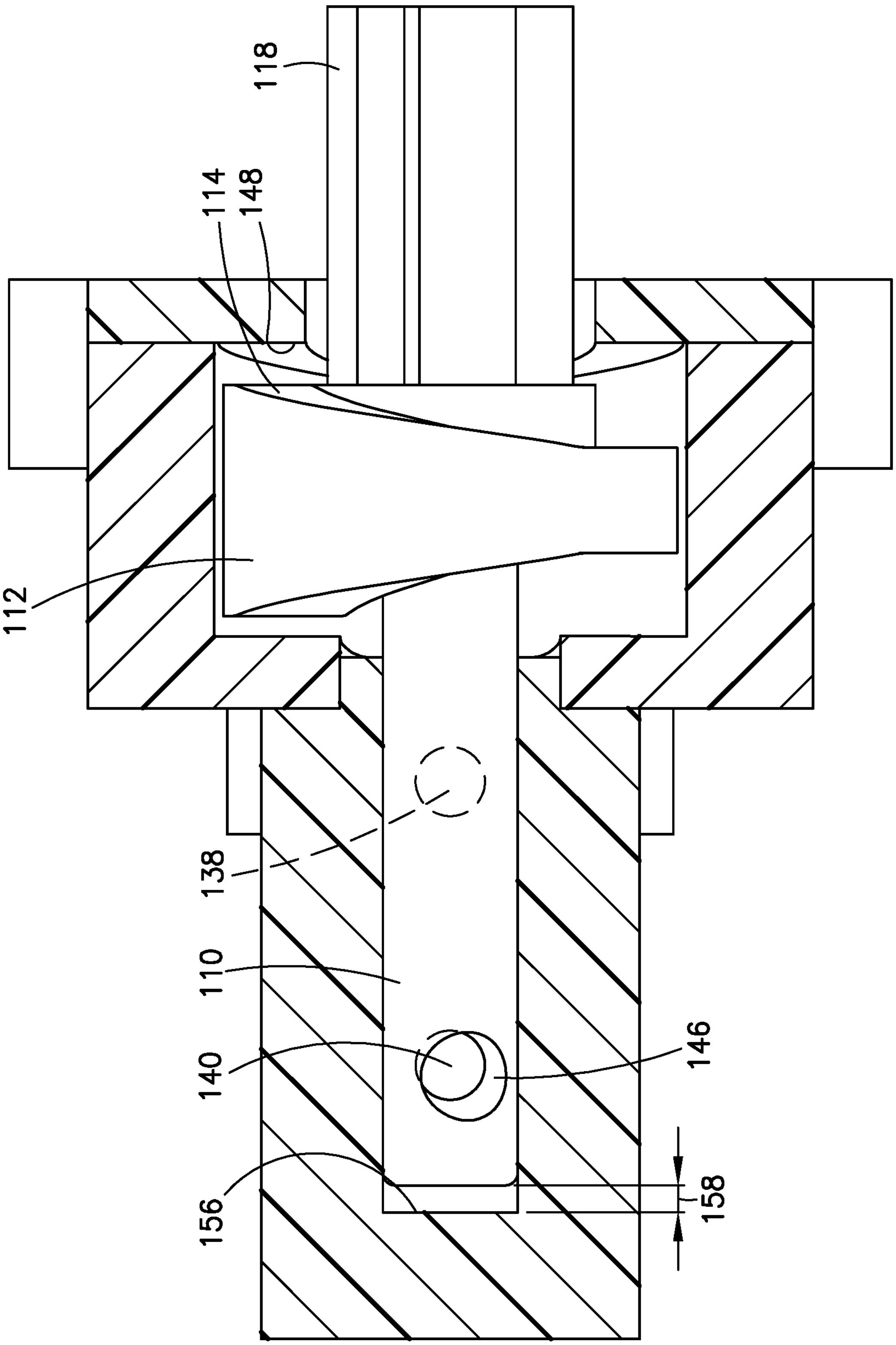
Figure 15:
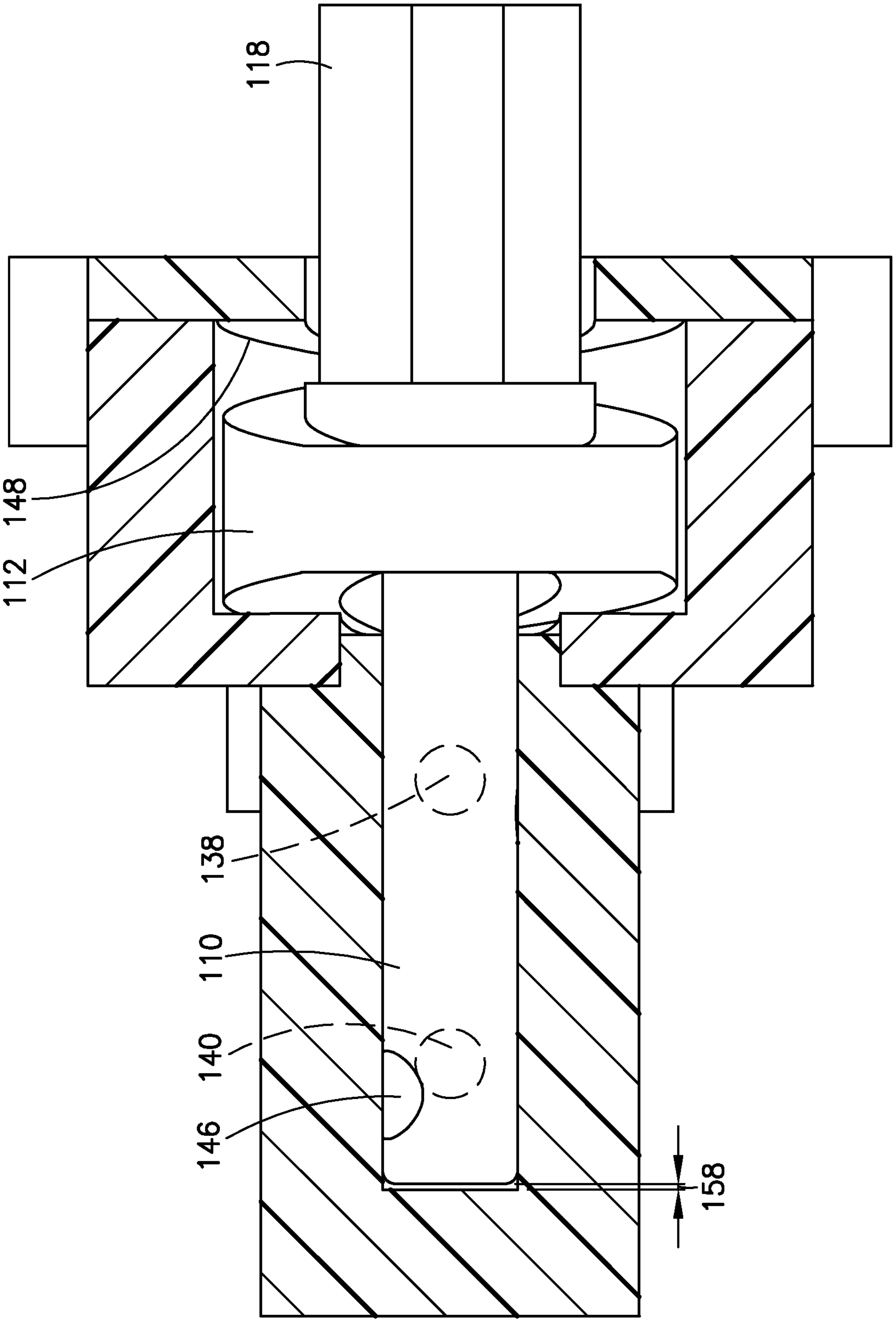

Turning now to FIGS. 9 through 15, the interaction and movement of the respective parts of the micro pump 100 will be described. In FIG. 9 the cam assembly is in a first position in which the cam 112 and cannula 110 are at their most distal position. Accordingly, in this position the volume of the manifold chamber 108 between a distal face of the manifold chamber 156 and a distal face of the stem 158 on the end of stem 142 (see FIG. 3). FIG. 10 illustrates cam assembly having been rotated to the beginning of an input portion of the movement. As can be seen cannula input hole 144 begins to overlap with input port 138 also due to interaction of the cam surface 116 with cam surface 150, cam 112 begins to move in a proximal direction as illustrated by the distance between end face 156 and the end of cannula 110 illustrated in FIG. 10 as reference number 158. FIG. 11 illustrates cam 112 rotated to a position where cannula hole 144 fully overlaps with input port 138. In addition, cam 112 has moved further distally causing the volume of the pump chamber to increase as illustrated by reference number 158. As the pump chamber volume increases liquid is drawn into manifold chamber 108 by vacuum. FIG. 12 illustrates cam 112 at the end of the input portion of the movement when the pump chamber volume within manifold chamber 108 is at a maximum as illustrated by reference number 158. In addition, cannula hole 144 stops overlapping input port 138. As shown in FIG. 13, cam 112 has rotated further and begins the output portion of the movement. The volume of manifold chamber 108 is still at a maximum and cannula hole 146 begins to overlap with output port 140. At this stage interaction, between cam surface 114 and cam chamber cap cam surface 148 begin to move the cannula 110 and a distal direction to reduce the volume of the manifold chamber 108. In FIG. 14 the cam assembly has rotated to a position in which cannula hole 146 fully overlaps output port 140. In addition, interaction between cam surface 114 and cam chamber cap cam surface 148 further translate the cam assembly in the distal direction, further lowering the volume of manifold chamber 108 as illustrated in reference number 158. Accordingly, liquid is forced out of manifold chamber 158 and into the output port 140. FIG. 15 illustrates the end of the output portion of the movement of cam 112. As illustrated, cannula output hole 146 moves past and stops overlapping with output port 140. The manifold chamber 108 volume is at a minimum as illustrated reference 158 and the cycle is ready to repeat.

While the present invention has been shown and described with reference to particular illustrative embodiments, it is not to be restricted by the exemplary embodiments but only by the appended claims and their equivalents. It is to be appreciated that those skilled in the art can change or modify the exemplary embodiments without departing from the scope of the present invention. In addition, the features of the various embodiments can be combined with each other to form new embodiments without departing from the scope of the present invention.

What is claimed is:

1. A pump for medical fluid comprising:

a pump housing;

a manifold within the pump housing, and having a manifold chamber therein, an input port and an output port;

a cannula received within the manifold chamber, and having an input hole and an output hole, arranged on opposite sides of the cannula and offset along an axis of the cannula to correspond with positions of the respective input port and output port of the manifold;

a cam received within a cam chamber, wherein the cam comprises a stem and the cannula is fixed to the stem, and adapted to cause the cannula to reciprocally translate in an axial direction a predetermined distance as the cam is rotated;

wherein the cannula is formed from metal needle stock having a predetermined gauge with a corresponding inner diameter, and the cannula reciprocates axially the predetermined distance to form a discrete pump volume between a distal face of the stem and a distal face of the manifold chamber and defined by the inner diameter of the cannula.

2. The pump of claim 1, wherein the cam chamber is formed from a cam chamber housing having a cam surface, and a cam chamber cap having a cam surface.

3. The pump of claim 2, wherein the cam chamber cap comprises an axial opening, and the cam comprises a motor coupling that extends through the cam chamber cap opening.

4. The pump of claim 3, wherein the motor coupling is slidably received within a motor portion.

5. The pump of claim 1, wherein the cam is arranged to cause the cannula input hole to align with the input port as the manifold chamber is increasing in size.

6. The pump of claim 1, wherein the cam is arranged to cause the cannula output hole to align with the output port as the manifold chamber is decreasing in size.

7. The pump of claim 1, wherein the cam comprises ramp surfaces that interact to move the cannula axially in a reciprocal manner as the cam rotates.

8. The pump of claim 1, wherein the input port and the output port are on the same side of the manifold chamber.

9. The pump of claim 1, wherein the input hole and the output hole are arranged such that only one of the input hole and output hole can be aligned with either of the input port or the output port at a given time.

10. A pump for medical fluid comprising:

a pump housing;

a manifold within the pump housing, and having a manifold chamber therein, an input port and an output port;

a cannula received within the manifold chamber, and having an input hole and an output hole, arranged on opposite sides of the cannula and offset along an axis of the cannula to correspond with positions of the respective input port and output port of the manifold;

a cam received within a cam chamber, wherein the cam is fixed to the cannula, and adapted to cause the cannula to reciprocally translate in an axial direction as the cam is rotated, wherein the cam chamber is formed from a cam chamber housing having a cam surface, and a cam chamber cap having a cam surface, and the cam chamber housing cam surface comprises a ramp shape.

11. A pump for medical fluid comprising:

a pump housing;

a manifold within the pump housing, and having a manifold chamber therein, an input port and an output port;

a cannula received within the manifold chamber, and having an input hole and an output hole, arranged on opposite sides of the cannula and offset along an axis of the cannula to correspond with positions of the respective input port and output port of the manifold;

a cam received within a cam chamber, wherein the cam is fixed to the cannula, and adapted to cause the cannula to reciprocally translate in an axial direction as the cam is rotated, wherein the cam chamber is formed from a cam chamber housing having a cam surface, and a cam chamber cap having a cam surface, and the cam chamber cap cam surface comprises a ramp shape.

* * * * *